United States Patent [19]

Gueremy et al.

[11] 4,224,332
[45] Sep. 23, 1980

[54] 1-AZA-[2,2,2]-BICYCLOOCTANES AND ANTI-DEPRESSANT AND ANTI-PARKINSONIAN COMPOSITIONS THEREOF

[75] Inventors: Claude G. A. Gueremy, Houilles; Francoise Hodac, Paris; Christian L. A. Renault, Epinay sur Seine, all of France

[73] Assignee: Pharmindustrie, Gennevilliers, France

[21] Appl. No.: 973,847

[22] Filed: Dec. 28, 1978

[30] Foreign Application Priority Data

Jan. 10, 1978 [FR] France ............................... 78 00490

[51] Int. Cl.$^2$ .................. A61K 31/445; C07D 453/02
[52] U.S. Cl. ................................... 424/267; 546/133
[58] Field of Search ......................... 546/133; 424/267

[56] References Cited

FOREIGN PATENT DOCUMENTS 2749584 5/1978 Fed. Rep. of Germany .
1235918 6/1960 France ..................................... 546/133

OTHER PUBLICATIONS

Houben-Weyl, Methoden der Organischen Chemie, vol. XIII/2a, p. 291, (1973), and vol. V./1a, Part 1, p. 227, (1970), Georg Thieme Verlag, Stuttgart, Germany.

*Primary Examiner*—John M. Ford
*Assistant Examiner*—Richard A. Schwartz
*Attorney, Agent, or Firm*—Beveridge, DeGrandi, Kline & Lunsford

[57] ABSTRACT

The compounds of the formula:

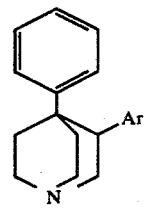

(I)

in which Ar is phenyl or phenyl substituted by 1 or 2 alkoxy groups, by a halogen atom or by a trifluoromethyl group are disclosed together with a process for the preparation thereof. These compounds are antidepressants and antiparkinson agents.

6 Claims, No Drawings

1-AZA-[2,2,2]-BICYCLOOCTANES AND ANTI-DEPRESSANT AND ANTI-PARKINSONIAN COMPOSITIONS THEREOF

The present invention relates to new derivatives of 1-aza-[2,2,2]-bicyclooctane, which can be used especially as psychotropic agents, more particularly as anti-depressants and anti-Parkinson agents.

The new derivatives may be represented by the formula:

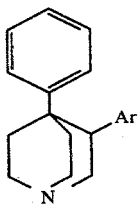
(I)

in which Ar represents a phenyl group, or a phenyl group substituted by 1 or 2 alkoxy groups, by a halogen atom or by a trifluoromethyl group. The alkoxy groups may contain from 1 to 4 carbon atoms, preferably from 1 to 3 carbon atoms. The halogen atom may be F, Cl, Br or I.

The products of formula (I) may be prepared by catalytic hydrogenation of the products of formula (II):

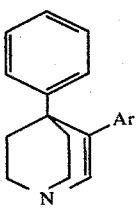
(II)

in which Ar has the same significance as in formula (I).

This reaction is effected in an inert solvent, for example an alcohol such as methanol or ethanol or an acid such as acetic acid, the product to be hydrogenated being used either in the form of the free base or in the form of a salt of the base.

The catalyst used is palladium, nickel, rhodium, ruthenium or platinum or an oxide of these three last metals. The reaction is effected under an atmosphere of hydrogen, at a temperature which may vary from 20° C. to 120° C.

A particularly good method for carrying out the catalytic hydrogenation of the compounds of formula (II) comprises operating in methanol, in the presence of palladium charcoal, under a pressure of hydrogen of 20 to 50 bars and at a temperature of about 50° C.

Once the hydrogenation has been completed, the reaction mixture is treated according to conventional methods, physical (evaporation, solvent extraction, distillation, crystallization, chromatography, etc.) or chemical (formation of a salt and regeneration of the base, etc.) in order to isolate the product of formula (I) in a pure state.

The products of formula (II) may be prepared by dehydration of the products of formula (III):

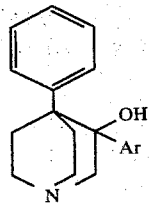
(III)

in which Ar has the same significance as in formula (I).

This reaction is effected by means of a suitable dehydrating agent, in the presence or in the absence of an inert solvent, according to methods known per se, for example those described by WAGNER and ZOOK (Synthetic Organic Chemistry, page 32, J. Wiley, 1965) which is relied upon herein for this purpose and the disclosure incorporated by reference. It is advantageously carried out by heating under reflux in the presence of an acid chloride such as thionyl chloride as dehydrating agent.

Once the reaction is finished, the reaction mixture is treated according to conventional methods (evaporation, treatment of the residue with water and extraction with a solvent, etc.) in order to isolate the products of formula (II) in a pure state, either in the form of the base or in the form of a salt of the base.

The products of formula (III) may be prepared by the action on the 4-phenyl-3-quinuclidinone [described by T. D. PERRINE, J. Org. Chem., 22, 1484 (1957)] of an organometallic derivative of formula Ar-M, in which M represents either a lithium atom or a group Mg-X (X being a halogen atom, generally bromine or iodine) and Ar has the same significance as in formula (I).

This reaction is carried out in an inert solvent such as an ether-oxide (ethyl ether or tetrahydrofuran), possibly mixed with other solvents such as hexamethylphosphotriamide or a hydrocarbon. The reaction is effected at a temperature from 0° C. to boiling temperature of the medium used. The reaction mixture is then treated with water, at low temperature and in the presence of an acid, and the compound of formula (III) formed is isolated by the usual methods.

The compounds of formulae (II) and (III) are new and form as such a part of the present invention.

The compounds of formula (I) in the form of the free base can be converted into salts of addition with a mineral or organic acid by the action of such acid in a suitable solvent. Suitable mineral acids include hydrofluoric, hydrochloric, hydrobromic hydroiodic, sulfuric, nitric and phosphonic acids. Suitable organic acids include formic, acetic, methanesulphoric fumaric, maleic, tantric and citric acids. Preferably the salts are pharmaceutically acceptable salts, i.e., salts of said compounds with a pharmaceutically acceptable acid. Preferably, the compounds are present in a pharmaceutically acceptable carrier therefor.

The solvents which may be used include ether, acetone, methanol, ethanol and isopropanol.

The following examples illustrate the invention without restricting it thereto. Examples 1 and 2 relate to the preparation of the compounds of formula (III), Example 3 to that of the compounds of formula (II) and Example 4 to that of the compounds of formula (I).

EXAMPLE 1

3,4-diphenyl-1-aza-[2,2,2]-bicyclo-3-octanol

A solution of 30 g of 4-phenyl-1-aza-[2,2,2]-bicyclo-3-octanone in 500 ml of tetrahydrofuran is added, at the ambient temperature, to 250 ml of a 2.4 M solution of phenylmagnesium bromide in tetrahydrofuran. The reaction mixture is maintained at 50° C. for 20 hours and is then poured on 2.7 kg of ice containing 150 ml of concentrated hydrochloric acid. It is decanted and the organic phase is distilled under reduced pressure in order to eliminate the tetrahydrofuran, which also causes the crystallization of the 3,4-diphenyl-1-aza-[2,2,2]-bicyclo-3-octanol hydrochloride. After washing with water and drying, 17.8 g of this product are obtained, of which the melting point is over 250° C.

The structure of the product obtained is confirmed by its infra-red spectrum (I.R.), which shows an absorption band at 3250 cm$^{-1}$ corresponding to the OH group.

EXAMPLE 2

3,4-diphenyl-1-aza-[2,2,2]-bicyclo-3-octanol

95 Ml of a 1.9 M solution of phenyllithium in a benzene-ether mixture is added, at 0° C. and in a period of 4 hours, to a solution of 12 g of 4-phenyl-1-aza-[2,2,2]-bicyclo-3-octanone in 360 ml of anhydrous tetrahydrofuran.

The reaction mixture is maintained for 1 hour at 0° C., then poured on 300 g of ice and 20 ml of concentrated hydrochloric acid. The tetrahydrofuran is eliminated by distillation under reduced pressure and sodium chloride is added to the aqueous suspension. The precipitate is filtered off and washed with water, then with ether and acetone. After drying, 12.2 g of 3,4-diphenyl-1-aza-[2,2,2]-bicyclo-3-octanol hydrochloride are obtained, of which the melting point is over 250° C. The structure of the product obtained is confirmed by its I.R. spectrum, which shows a band of absorption at 3250 cm$^{-1}$ corresponding to the OH group.

EXAMPLE 3

3,4-diphenyl-1-aza-[2,2,2]-bicyclo-2-octene

A solution of 16.8 g of 3,4-diphenyl-1-aza-[2,2,2]-bicyclo-3-octanol hydrochloride in 425 ml of thionyl chloride is refluxed for 3 hours. Then the solution is concentrated under reduced pressure and the compound formed is precipitated by addition of toluene. After washing with ether and drying the precipitate, 15.7 g of 3,4-diphenyl-1-aza-[2,2,2]-bicyclo-2-octene hydrochloride melting at 245° C. are obtained.

Analysis for: $C_{19}H_{19}N$, HCl

|  | %C | %H | %N |
|---|---|---|---|
| Calculated: | 76.7 | 6.72 | 4.71 |
| Found: | 76.8 | 6.9 | 4.7 |

EXAMPLE 4

3,4-diphenyl-1-aza-[2,2,2]-bicyclooctane 7.4 G of 3,4-diphenyl-1-aza-[2,2,2]-bicyclo-2-octene hydrochloride in solution in 75 ml of methanol is hydrogenated for 7 hours in the presence of 1.8 g of palladium charcoal, at 50° C. and under a pressure of hydrogen of 30 bars. After filtration, then removal of the solvent under reduced pressure, 7 g of product are obtained which is recrystallized in 25 ml of absolute ethanol. 4.5 G of 3,4-diphenyl-1-aza-[2,2,2]-bicyclooctane hydrochloride are obtained of which the melting point is over 230° C.

Analysis for: $C_{19}H_{21}N$, HCl, $\frac{1}{2}$ $H_2O$

|  | %C | %H | %N | %Cl |
|---|---|---|---|---|
| Calculated: | 73.8 | 7.45 | 4.52 | 11.5 |
| Found: | 72.1 | 7.3 | 4.2 | 11.1 |

PHARMACOLOGICAL PROPERTIES

(1) ACTION OF THE PRODUCTS ON HYPOTHERMIA CAUSED BY RESERPINE IN MICE

The efficiency of the compounds of the present invention as antidepressants has been demonstrated by means of the hypothermia test with reserpine in mice, according to the method of D. M. ASKEN, Life Sciences 1963, Vol. 2, p. 725.

The results are expressed by an $ED_{50}$ or dose of product, in mg/kg, capable of exerting an antihypothermic effect equal to 50% of the antihypothermic effect caused by 15 mg/kg (per os) of imipramine.

The following Table 1 gives by way of example the result obtained with the compound of Example 4:

TABLE 1

| Product | $ED_{50}$ p.o. |
|---|---|
| Example 4 | 2 |
| Imipramine | 3 |

(2) ACTION OF THE PRODUCTS ON THE UPTAKE OF THE CEREBRAL MONOAMINES

It is known that the antidepressant products known at present have the property of inhibiting the uptake of the cerebral monoamines.

The activity of the products according to the present invention as antidepressants has now been shown, in vitro, by means of the test for inhibition of the uptake of the cerebral amines by the synaptosomes of the rat's brain, according to the method of KANNENGIESSER et al., (Biochem. Pharmacol. 22, 73, 1973) which is relied upon herein for this purpose and the disclosure incorporated by reference.

The results are expressed by an inhibiting concentration $IC_{50}$, which represents the dose of product in micromoles per liter reducing by 50% the uptake of the noradrenaline (NA), the dopamine (DA), the serotonine (5-HT), or the choline in the specific regions of the brain (hypothalamus, striatum, medulla+pons) where the corresponding neurons predominate.

The results obtained with the product of Example 4 are given by way of example in the following Table 2. In this table are also given for comparison the results obtained with three antidepressants of reference (amphetamine, nomifensine and imipramine).

TABLE 2

| | $IC_{50}$ | | | |
|---|---|---|---|---|
| Product | NA (Hypothalamus) | DA (Striatum) | 5-HT (Medulla + pons) | CHOLINE (Striatum) |
| Amphetamine | 0.012 | 1.7 | 5 | 1000 |
| Nomifensine | 0.022 | 0.65 | 4 | 1000 |
| Imipramine | 0.13 | 55 | 0.08 | 30 |

TABLE 2-continued

| | IC$_{50}$ | | | |
|---|---|---|---|---|
| Product | NA (Hypo-thalamus) | DA (Striatum) | 5-HT (Medulla + pons) | CHOLINE (Striatum) |
| Example 4 | 0.045 | 0.60 | 0.30 | 25 |

The product of Example 4 is active on all the four mediators used. Its inhibiting effect is near to that of the imipramine as far as NA, 5-HT and choline are concerned, but is very superior to that of imipramine concerning the uptake of the dopamine at the level of the striatum.

On this last point the product of Example 4 comes near to the nomifensine, but it exerts on the neuronal uptake of the choline an inhibiting activity which the nomifensine does not possess.

These two joint inhibiting effects on the uptake of the dopamine and the choline give evidence of the central prodopaminergic and anticholinergic properties of the compounds of formula (I) which properties are connected with the application of these compounds to the treatment of Parkinson's disease [cf. The Pharmacotherapy of Parkinsonism - R. M. PINDER - Progress in Medicinal Chemistry 9, 191 (1973)], which is relied upon herein and the disclosure incorporated by reference.

TOXICOLOGICAL PROPERTIES

The acute toxicities of the compounds of formula (I) have been determined on the male mouse CD$_1$ (Charles River), the products being administered orally. The LD$_{50}$ have been calculated, after 3 days observation, by the cumulative method of J. J. REED and H. MUENCH. (Amer. J. Hyg. 27, 493, 1938), which is relied upon herein for this purpose and the disclosure incorporated by reference.

The compounds of formula (I) are substances which have relatively little toxicity to mice. By way of example, the LD$_{50}$ is 200 mg/kg for the compound of Example 4.

THERAPEUTIC USE

The compounds of formula (I) and their pharmaceutically acceptable salts may be used in human therapeutics in the form of compressed tablets, capsules, gelatin-coated pills, suppositories, ingestable or injectable solutions, etc., for the treatment of the depressive states and as antiparkinson medicaments.

The posology depends on the effects required and the method of administration used. For example, taken orally, from 5 to 100 mg of active substance per day may be used, with single doses ranging from 1 to 20 mg.

What is claimed is:

1. A compound of the formula:

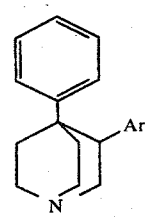

(I)

in which Ar represents an unsubstituted phenyl group or a phenyl group substituted by 1 or 2 alkoxy groups having from 1 to 4 carbon atoms or by a halogen atom or by a trifluoromethyl group, or a salt of addition of said compound with a pharmaceutically acceptable acid.

2. A compound according to claim 1 in which Ar is an unsubstituted phenyl group.

3. A compound of the formula:

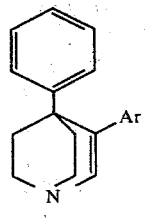

(II)

in which Ar has the same significance as in claim 1.

4. A compound of the formula:

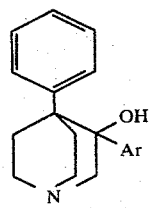

(III)

in which Ar has the same significance as in claim 1.

5. A composition, particularly useful as an antidepressant and antiparkinson agent, which contains as active principle a pharmaceutically effective amount of a compound of claim 1 or a salt of said compound with a pharmaceutically acceptable acid, in a pharmaceutically acceptable carrier therefor.

6. A composition according to claim 5 which contains as active principle 3,4-diphenyl-1-aza-[2,2,2]-bicyclooctane or a salt of this compound with a pharmaceutically acceptable acid.

* * * * *